US005538653A

United States Patent [19]

Avery et al.

[11] Patent Number: 5,538,653
[45] Date of Patent: Jul. 23, 1996

[54] FRICTION MODIFIERS AND ANTIWEAR ADDITIVES FOR FUELS AND LUBRICANTS

[75] Inventors: Noyes L. Avery, Bryn Mawr, Pa.; James T. Carey, Medford, N.J.; John Hiebert, Levittown, Pa.; Andrew G. Horodysky, Cherry Hill, N.J.

[73] Assignee: Mobil Oil Corporation, Fairfax, Va.

[21] Appl. No.: 444,977

[22] Filed: May 19, 1995

Related U.S. Application Data

[62] Division of Ser. No. 245,275, May 18, 1994, Pat. No. 5,482,521.

[51] Int. Cl.$^6$ ............................................. C10M 133/38
[52] U.S. Cl. ................................................ 508/229
[58] Field of Search ......................... 252/51.5 R, 51.5 A

[56] References Cited

U.S. PATENT DOCUMENTS

| | | | |
|---|---|---|---|
| 4,153,564 | 5/1979 | Chibrik | 252/51.5 A |
| 4,187,186 | 2/1980 | Braid | 252/51.5 A |
| 4,897,086 | 1/1990 | Blain et al. | 252/51.5 A |
| 4,963,278 | 10/1990 | Blain et al. | 252/51.5 A |
| 5,133,890 | 7/1992 | O'Neil et al. | 252/51.5 R |
| 5,271,856 | 12/1993 | Patil et al. | 252/51.5 R |
| 5,328,625 | 7/1994 | Farng et al. | 252/51.5 R |
| 5,348,674 | 9/1994 | Blain et al. | 252/51.5 R |
| 5,407,592 | 4/1995 | Cheng et al. | 252/51.5 R |
| 5,482,521 | 1/1996 | Avery et al. | 44/344 |

*Primary Examiner*—Ellen M. McAvoy
*Attorney, Agent, or Firm*—Ronald A. Bleeker; Malcolm D. Keen; Gerald L. Harris

[57] ABSTRACT

The invention relates to lubricant and fuel additives having antiwear and friction reducing properties. The invention also relates to compositions of oils with viscosities appropriate for lubricants, greases produced therefrom, and fuels and methods for making these compositions. Described in this invention are products of nitrogen heterocycles, such as benzotriazole and tolyltriazole, with amines, such as alkyl amines, aliphatic diamines, alicyclic amines, heterocyclic amines, propylene amines, and aliphatic etheramines, that are linked using carbonyl compounds (e.g., aldehyde, ketone or glyoxal). Additionally, products generated by the reaction of carboxylic acids or carboxylic acid generating compounds (e.g., salts or esters) with carbonyl (e.g., aldehyde, ketone or glyoxal) coupled nitrogen heterocycles and amines, including those described above, are also included in this invention. These products can be used in fuels and lubricants to produce improved antiwear and friction reducing properties.

22 Claims, No Drawings

5,538,653

FRICTION MODIFIERS AND ANTIWEAR ADDITIVES FOR FUELS AND LUBRICANTS

CROSS-REFERENCE TO RELATED APPLICATIONS

This is a division of application Ser. No. 08/245,275, filed on May 18, 1994, now U.S. Pat. No. 5,482,521.

FIELD OF THE INVENTION

The invention relates to lubricant and fuel additives having antiwear and friction reducing properties. The invention also relates to compositions of oils with viscosities appropriate for lubricants, greases produced therefrom, as well as fuels and methods for making these compositions.

BACKGROUND OF THE INVENTION

Tolyltriazole and alkyl amines linked by formaldehyde are known to provide antiwear properties in fuels and lubricants. Katritzky, Fan, and Fu (Alan R. Katritzky, Wei-Qiang Fan, and Cong Fu, *J. Org. Chem.*, 1990, 55, 3209–3213) describe syntheses in which a nitrogen heterocycle, benzotriazole, is linked to primary and/or secondary amines using glyoxal.

SUMMARY OF THE INVENTION

This invention includes products of nitrogen heterocycles, such as benzotriazole and tolyltriazole, with amines, such as alkyl amines, aliphatic diamines, alicyclic amines, heterocyclic amines, propylene amines and aliphatic etheramines, that are linked using carbonyl compounds (e.g., aldehyde, ketone or glyoxal). Whereas some of the products themselves may be related to Katritzky, Fan, and Fu's work, the fuel and lubricant compositions of these products and the unexpected but excellent antiwear and friction reducing properties of these compositions are unique. These remarkable benefits are expected for a variety of fuel compositions and for a variety of synthetic, mineral oil, and vegetable oil based lubricants. Additionally, other additives generated by the reaction of carboxylic acids or carboxylic acid generating compounds (e.g., salts or esters) with carbonyl (e.g., aldehyde, ketone or glyoxal) coupled nitrogen heterocycles and amines, including those described above, can be used in fuels and lubricants to produce improved antiwear and friction reducing properties. In addition to antiwear and friction reducing properties, antioxidant, high temperature stabilizing, anticorrosion, antistaining, metal deactivation, cleanliness, detergency/dispersancy, antifatigue, extreme pressure, and demulsifying/emulsifying properties are likely with many of the embodiments of this invention.

One embodiment of this invention is a compound comprising the reaction product of at least one nitrogen heterocycle, at least one amine, at least one carbonyl compound, and, optionally, at least one carboxyl compound.

Another embodiment is a lubricant or fuel additive comprising the reaction product of at least one nitrogen heterocycle, such as tolyltriazole, at least one amine, and at least one glyoxal.

Yet another embodiment of this invention is a lubricant or a fuel composition comprising a major amount of oil with viscosity suitable for use as a lubricant, grease produced therefrom, or a fuel and a minor amount of an additive comprising the reaction product of at least one nitrogen heterocycle, at least one amine, and at least one glyoxal.

A further embodiment of this invention is a lubricant or a fuel composition comprising a major amount of oil with viscosity suitable for use as a lubricant, grease produced therefrom, or a fuel and a minor amount of an additive comprising the reaction product of at least one nitrogen heterocycle, at least one amine, at least one carbonyl compound, and, optionally, at least one carboxyl compound or carboxyl generating compound.

Another embodiment of this invention is a method of making a lubricant or a fuel comprising incorporating a major amount of oil with viscosity suitable for use as a lubricant, grease produced therefrom, or a fuel with a minor amount of an additive comprising the reaction product of at least one nitrogen heterocycle, at least one amine, and at least one carbonyl, such as glyoxal. An optional variation of this embodiment is one in which at least one carboxyl compound is included in the reaction product.

DETAILED DESCRIPTION OF THE INVENTION

The instant invention is directed to additives which are soluble in fuels or lubricants; less soluble embodiments can be used in greases or other solid lubricants. An additive has been discovered which has improved antiwear and friction reducing properties when incorporated into lubricating oils and fuels comprising the reaction product of a carbonyl, such as glyoxal, a nitrogen heterocycle and an amine selected from the group consisting of an alkyl amine, aliphatic diamine, alicyclic amine, heterocyclic amine, propylene amine and aliphatic etheramine. A carboxylic acid or a carboxylate forming compound may be also included in the reaction product.

One embodiment of this invention is a compound comprising the reaction product of at least one nitrogen heterocycle, at least one amine, at least one carbonyl compound, and at least one carboxyl compound.

An additional embodiment of this invention is a compound comprising the reaction product of at least one nitrogen heterocycle, such as tolyltriazole, at least one amine, and at least one glyoxal.

Another embodiment of this invention is a lubricant or a fuel composition comprising a major amount of oil with viscosity suitable for use as a lubricant, grease produced therefrom, or a fuel and a minor amount of an additive comprising the reaction product of at least one nitrogen heterocycle, at least one amine, and at least one glyoxal.

Yet another embodiment of this invention is a lubricant or a fuel composition comprising a major amount of oil with viscosity suitable for use as a lubricant, grease produced therefrom, or a fuel and a minor amount of an additive comprising the reaction product of at least one nitrogen heterocycle, at least one amine, at least one carbonyl compound, and at least one carboxyl compound or carboxyl generating compound.

Another embodiment of this invention is a method of making a lubricant or a fuel comprising blending a major amount of oil with viscosity suitable for use as a lubricant, grease produced therefrom, or a fuel with a minor amount of an additive comprising the reaction product of at least one nitrogen heterocycle, at least one amine, and at least one carbonyl, such as glyoxal. A variation of this embodiment is one in which at least one carboxyl compound is included in the reaction product.

The nitrogen heterocycle is a 5-membered ring structure in which three of the ring members are nitrogen, the other ring members can be oxygen, sulfur or carbon atoms. Typical nitrogen heterocycles are triazoles, especially those already known for their antioxidant characteristics. The triazole is characterized by the following structural formula:

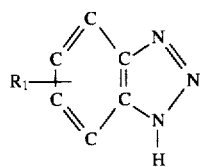

where $R_1$ is hydrogen or an alkyl group containing 1 to 60 carbon atoms or an alkyl group containing 2 to 60 carbon atoms and at least one heteroatom which is oxygen, sulfur, nitrogen and combinations thereof. Representative examples of alkyl groups include methyl, ethyl, propyl, butyl, pentyl, hexyl, heptyl, octyl, nonyl, decyl, dodecyl, polyisobutyl, polyisobutenyl, oligomeric decene, and polyisopropylene or any combination thereof. Non-limiting examples of suitable triazoles include tolyltriazole, where $R_1$ is methyl, ethylbenzotriazole, propylbenzotriazole, butylbenzotriazole, the higher benzotriazoles such as dodecylbenzotriazole and oxygenated benzotriazoles such as carboxymethylbenzotriazole. The triazoles are known in the art and can be obtained from commercial sources.

The carbonyl compound can be any compound containing the group (C=O) which occurs in aldehydes and ketones. This compound can be characterized by the structural formula

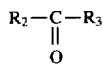

in which $R_2$ and $R_3$ independently are hydrogen or linear, branched or cyclic hydrocarbyl or hydrocarbylene generally containing 1 to 200 carbon atoms, specifically 1 to 60 carbon atoms, which are alkyl, aryl, arylalkyl or alkylaryl. The hydrocarbyl or hydrocarbylene group can also generally contain 2 to 200 carbon atoms, specifically 2 to 60 carbon atoms, and at least one heteroatom which can be oxygen, sulfur or nitrogen. Non-limiting examples of typical carbonyl compounds include formaldehyde, heptaldehyde, hexaldehyde, acetaldehyde, propionaldehyde, paraformaldehyde, benzaldehyde, salicylaldehyde, acetone, diethyl ketone, methyl ethyl ketone and 2-ethylhexanal. Also included in this definition and useful in this invention are dicarbonyl compounds, including dialdehydes, such as glutaraldehyde. These compounds are known in the art and are readily available from commercial sources or are easily made using known methods.

The carbonyl compound may also be a glyoxal which may be characterized by the formula $R_2COR_3CO$ where $R_2$ and $R_3$ are as defined above. One commercially available form is glyoxal.

The nitrogen heterocycle and the carbonyl compound are reacted with at least one amine which can be an alkyl amine, long-chain aliphatic amine, branched chain aliphatic amine, alicyclic amine, heterocyclic amine, aliphatic diamine, aliphatic triamine, propylene amine, oxygenated amine, aliphatic etheramine, ether diamine, polyether primary amine, hydroxyl-containing amine and mixtures thereof.

Also polyethylene amines such as ethylene diamine, diethylene triamine, triethylene tetramine, tetraethylene pentamine and mixtures thereof, higher oligomers thereof, hydrocarbyl substituted polyethylene amine, and all of the corresponding polypropylene amines and polybutylene amines and their homologues and mixtures may be used.

The alkyl amines are amines designated by the following structure:

$R_4NR_5R_6$ in which $R_4$, $R_5$ or $R_6$ is, independently, a hydrogen atom in the case of a primary or secondary amine, or $R_4$, $R_5$ and $R_6$ are the same or different hydrocarbon groups, and where at least one of $R_4$, $R_5$ or $R_6$ must be hydrogen. $R_4$, $R_5$ or $R_6$ is generally a hydrocarbyl or hydrocarbylene group generally containing 1 to 200 carbon atoms, specifically 1 to 60 carbon atoms and can contain at least one heteroatom which is oxygen, sulfur, nitrogen and combinations thereof, and, generally, 2 to 200 carbon atoms, specifically 2 to 60 carbon atoms. Non-limiting examples of the alkyl amines include the straight chain monoamines such as methyl ethyl amine, propylamine or butylamine. The particularly preferred amines are the long-chain aliphatic amines such as pentylamine, hexylamine, octylamine, dioctylamine, dicocoamine, dioleylamine and the like. The term "long chain" designates the amines containing hydrocarbyl groups of $C_5$ and higher, preferably over $C_8$ and in the range of $C_5$ to $C_{22}$ or more, preferably $C_8$ to $C_{20}$. The branched chain amines include, but are not limited to, the short chain amines, i.e., isopropylamine, isobutylamine, diisobutylamine and longer chain branched amines such as 2-ethylhexylamine and bis(2-ethylhexyl)amine. The term "short chain amines" designates amines containing hydrocarbon groups of $C_5$ and lower, preferably $C_3$ and lower.

Non-limiting examples of the alicyclic amines are dicyclohexylamine, 1,4-diaminocyclohexane, piperidine and hexamethyleneimine.

The contemplated amines are also heterocyclic in which the nitrogen atom is an integral member of a ring structure which is predominantly composed of carbon atoms. Suitable, but not limiting examples of heterocyclic amines include morpholine, aminopropylmorpholine (APM) and aminoethylpiperazine (AEP).

The aliphatic diamines are also used. In general the long-chain diamines are contemplated and have the structural formula:

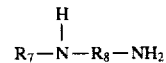

where $R_7$ is an alkylene group containing 10 to 30 carbon atoms and $R_8$ is an alkylene group containing 2 to 4 carbon atoms. Some non-limiting examples of diamines include N-tallow-1,3-propylenediamine, N-oleyl-1,3-propylenediamine, N-linoleyl- 1,3-propylenediamine, N-stearyl-1,3-propylenediamine, N-soya- 1,3-propylenediamine, N-cocoyl-1,3-diaminopropane, N-oleyl- 1,3-diaminopropane, N-isostearyl-1,3-propylenediamine, N-tallow- 1,2-ethylenediamine, N-oleyl-1,2-ethylenediamine, N-linoleyl- 1,2-ethylenediamine, N-stearyl-1,2-ethylenediamine, N-soya-1,2-ethylenediamine, N-cocoyl-1,2-diaminoethane, N-oleyl-1,2-diaminoethane, N-isostearyl-1,2-ethylenediamine, and mixtures of two or more of these amines.

Aliphatic triamines may also be used. In general, aliphatic triamines having the following formula are contemplated:

$R_9NH(CH_2CH_2CH_2)NH(CH_2CH_2CH_2)NH_2$ where $R_9$ is selected from hydrogen or $C_1$–$C_{20}$ linear, branched, or cyclic hydrocarbyl or hydrocarbylene group. The hydrocarbyl or hydrocarbylene group can also contain 2 to 20 carbon atoms and at least one heteroatom which can be oxygen, sulfur, nitrogen, and combinations thereof. Non-limiting examples of these amines include diethylene triamine, triamino propane, N,N'-di(2-aminoethyl)-amine, bis(hexamethylene) triamine, pentamethyl diethylenetriamine, 2,2-dimethyldiethylenetriamine, N1-tert. butyl-1,2,3-triaminopropane, 2,2,5,5-tetramethyl diethylenetriamine, 1,3,6-triaminomethylhexane, 1,2,3-triaminoethylpropane, 4-aminomethyl-octamethylenediamine, 3,3'-diamino-dipropylamine, spermidine, 4,4'-diamino-dibutylamine, 6,6'diaminohexylamine, 2,4-bis(4-aminocyclohexylmethyl)cyclohexylamine.

Propylene amines may also be used. These amines are typified by the following structure:

where x is 0 to 10, and $R_{10}$, $R_{11}$, $R_{12}$, and $R_{13}$ are independently selected from hydrogen, or generally $C_1$–$C_{200}$, specifically $C_1$–$C_{60}$ linear, branched or cyclic hydrocarbyl or hydrocarbylene. The hydrocarbyl or hydrocarbylene group can also generally contain 2 to 200 carbon atoms, specifically 2 to 60 carbon atoms, and at least one heteroatom which can be oxygen, sulfur, nitrogen, and combinations thereof.

The oxygenated amines are also suitable. The oxygenated amines contemplated include the aliphatic etheramines such as the alkoxypropylamines having the structural formula

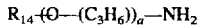

where a is 1 to 20 and in which $R_{14}$ is an alkyl group which contains 4 to 20 carbon atoms, preferably 6 to 18 carbon atoms. Non-limiting examples of the alkoxypropylamines include 3-methoxypropylamine, 3-ethoxypropylamine, 3-propyloxypropylamine, 3-butyloxy-propylamine, 3-octyloxypropylamine, 3-hexoxypropylamine, 3-heptoxypropylamine, 3-nonyloxypropylamine and 3-decyloxypropylamine.

The ether diamines are another class of oxygenated amines which are suitable. Non-limiting examples of the ether diamines are those having the structure:

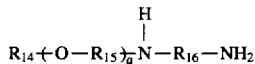

Where a is 1 to 20 and $R_{14}$ is as defined above, but where $R_{14}$ preferably contains 6 to 18 carbon atoms arranged in a straight or branched chain configuration. $R_{15}$ is an alkyl group containing 2 to 4 carbon atoms, $R_{16}$ is an alkyl group having at least 2 to 3 carbon atoms, at most 5 to 10 carbon atoms. Non-limiting examples of ether diamines include hexoxypropyl-1,3-propylenediamine, heptoxypropyl-1,3-propylenediamine, octoxypropyl-1,3-propylenediamine and nonoxypropyl-1,3-propylenediamine and any mixtures of the foregoing ether diamines.

The polyether primary amines are also contemplated. Suitable polyether primary amines have the following structural formula

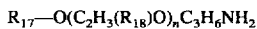

where $R_{17}$ is an alkyl-substituted phenyl group containing 14 to 26 carbon atoms, $C_6$ to $C_{30}$ alkyl group or $C_7$ to $C_{30}$ aralkyl group, n is an integer ranging from 2 to 10 and $R_{18}$ is independently hydrogen or methyl. These alkyl-substituted phenol-derived polyetheramines are sold by Texaco Chemical Co. under the trademark Surfonamine. Those available commercially include:

| Trademark | Structure |
|---|---|
| Surfonamine MNPA-380 | nonylphenyl-1EO—2PO—NH$_2$ |
| Surfonamine MNPA-510 | nonylphenyl-4EO—2PO—NH$_2$ |
| Surfonamine MNPA-750 | nonylphenyl-9.5EO—2PO—NH$_2$ |
| Surfonamine MNPA-860 | nonylphenyl-12EO—2PO—NH$_2$ |

Contemplated polyether primary amines are those derived from nonylphenol ethoxylates such as where $R_{17}$ is nonylphenyl. Specific examples of these polyether primary amines include the compounds sold by Texaco under the tradename SURFONAMINE MNPA.

In general, hydroxyl-containing amines having the following formula are also contemplated as oxygenated amines:

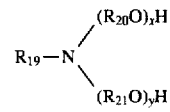

where x and y are integers from 1 to 10 and the sum of x+y is at least 1 and $R_{19}$ is selected from hydrogen or generally $C_1$–$C_{200}$, specifically $C_1$–$C_{60}$ linear, branched, or cyclic hydrocarbyl or hydrocarbylene group, and where $R_{20}$ and $R_{21}$ are independently selected from $C_2$–$C_{10}$ hydrocarbylene oxide. The $R_{19}$ hydrocarbyl or hydrocarbylene group can also generally contain 2 to 200 carbon atoms, specifically 2 to 60 carbon atoms, and at least one heteroatom which can be oxygen, sulfur, nitrogen and combinations thereof. Non-limiting examples of hydrocarbylene oxides include ethylene oxide and styrene oxide.

The nitrogen heterocycle, the carbonyl compound and the amine can be reacted together in any sequence. However, for illustrative purposes, the carbonyl compound is added to a solvated mixture of the nitrogen heterocycle and the amine. The nitrogen heterocycle and the carbonyl compound are typically reacted in an equimolar proportion such that one equivalent amount of the carbonyl compound is used for each equivalent amount of the nitrogen heterocycle and the amine. However, the invention is also effective when the components are not added in equimolar proportions. In other words, an excess of any component may be added to the reaction mixture without compromising the effectiveness of the invention. The reaction is a condensation reaction in which water is formed as the product evolves. The amount of water produced by the reaction may be used to monitor the course of reaction: one mole of water is typically formed for each mole of product formed.

The reaction is carried out at a temperature of less than 50° C., preferably less than 40° C., which increases to at least 60° C. to 70° C., at most 110° C. to 150° C. during the course of the reaction. After the reactants have been contacted for at least 10 minutes to 1 hour, typically about 3 hours to about 48 hours, specifically about 6 hours to about 24 hours, any solvent used to facilitate the reaction and any water present which is produced by the reaction may be removed, usually by azeotropic and/or vacuum distillation. The solvent is not required to be removed before use of these reaction products according to this invention. A solvent or diluent inert to the reactants can be used to facilitate the reaction and which provide good solubility for the triazole.

Non-limiting examples of suitable solvents include methanol, ethanol, isopropyl alcohol, butanol and other similar alcohols. A co-solvent may also be used. Non-limiting examples of co-solvents include toluene, benzene, xylene, hexane, cyclohexane and similar compounds, and mixtures of similar compounds.

The reaction product is optionally treated with a carboxylic acid or carboxylate forming compound, such as a salt or an ester of a carboxylic acid to form a further reaction product comprising partial, single or multiple salts or covalent carboxylates or a mixture thereof. Carboxylic acids that may be used typically have the following structure:

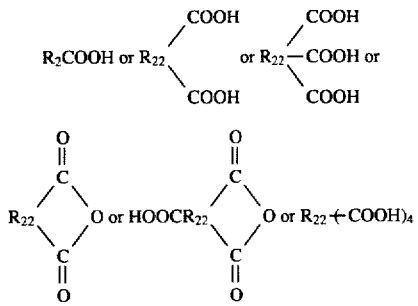

where $R_{22}$ is hydrogen or $C_1$–$C_{30}$ linear, branched, aliphatic, aromatic, or alkylaromatic or cyclic hydrocarbyl or hydrocarbylene or a mixture thereof. The hydrocarbyl or hydrocarbylene group can also generally contain 2 to 30 carbon atoms, and at least one heteroatom which can be oxygen, sulfur or nitrogen. Non-limiting examples of suitable carboxylic acids include oleyl, linoleic, dimer and sarcosine carboxylic acids. Non-limiting examples of suitable carboxylic acid forming compounds include succinic, phthalic, trimellitic, benzene tetracarboxylic, and benzophenone anhydrides. Linear or branched fatty acids are often preferred.

As mentioned above, the nitrogen heterocycle, carbonyl, amine, and optional carboxyl compounds may be reacted together in any order. One possible sequence is the combination of the nitrogen heterocycle, carbonyl, and amine group in any order, followed by the addition of the carboxyl if desired.

Fuel and lubricant compositions containing additives made from the above reaction products have improved antiwear and friction reducing properties. It is believed that the nitrogen heterocycle, the amine, and the carboxylate components (when present) provide the basis for the synergistic friction reduction and antiwear properties provided by these novel additives.

All of the above described beneficial properties are believed to be enhanced as a result of this novel internal synergism. This unique synergism concept is believed to be applicable to similar structures containing single or multiple combinations of groups within the same molecule including nitrogen heterocycles, amines, and, optionally, carboxylic acids. Products made according to this invention show good stability and compatibility when used in the presence of other commonly used additives in fuel and lubricant applications. Some products may have demulsive properties. Significant improvements in vehicle fuel economy benefits and longer engine service lifetimes are expected. With the use of such additives in fuels, reduced pollution, as measured by hydrocarbon, carbon monoxide, and $NO_x$ emissions, is also expected.

The reaction products are blended with lubricants in a concentration of about 0.01% to 10%, preferably, from 0.05% to 5% by weight of the total composition.

As previously mentioned, the additives are suitable for use in engine oils and gear oils. The engine oils which will benefit from these additives include oils for gasoline and alternative fuel burning engines and diesel engines. The contemplated gear oils which will benefit from the additives are hypoid gear oils which are exposed to the most severe service conditions. Other gear oils contemplated include automotive spiral-bevel and worm gear axle oils.

Although the additives are successful in internal combustion engine oils and gear oils, it is contemplated that the additives will successfully perform in other functional fluids and industrial lubricants. Other lubricant applications contemplated include the use of the instant additives in circulation oils and steam turbine oils, gas turbine oils (both heavy-duty gas turbines and aircraft gas turbines), machine tool lubricants and hydraulic fluids.

The contemplated lubricants are liquid oils in the form of either a mineral oil or synthetic oil or mixtures thereof. Also contemplated are greases in which any of the foregoing oils are employed as a base. Still further materials which it is believed would benefit from the reaction products of the present invention are plastic materials.

In general, mineral oils, paraffinic, naphthenic, aromatic and mixtures thereof can be employed as a lubricating oil or as the grease vehicle. The lubricating oils can be of any suitable lubrication viscosity range, for example, from about 45 SSU at 100° F. to about 6000 SSU at 100° F., and preferably from about 50 to 250 SSU at 210° F. Viscosity indexes range from about 70 and higher, preferably 90 to 130. The average molecular weights of these oils can range from about 250 to about 800.

The additives of this invention are also effective in food-grade oils, such as vegetable oils or their derivatives.

It is also desirable to employ the additive in greases. The additive is particularly useful when used in gear greases. However, other classes of greases which will benefit from the additive include greases for automobile chassis lubrication, greases for journal and wheel bearings, etc. Typically, the range of application includes the automotive industry, railways and aviation industries.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in amounts sufficient to impart to the resulting grease composition the desired consistency. Other thickening agents that can be employed in the grease formulation comprise the non-soap thickeners, such as surface-modified clays and silicas, aryl ureas, calcium complexes, and similar materials. In general, grease thickeners can be employed which do not melt or dissolve when used at the required temperature within a particular environment. However, in all other respects, any material which is normally employed for thickening or gelling hydrocarbon fluids for forming greases can be used with the present invention.

Where synthetic oils, or synthetic oils employed as the vehicle for the grease are desired in preference to mineral oils, or mixtures of mineral and synthetic oils are desired, various synthetic oils may be used. Typical synthetic oils include the polyalphaolefins, polypropylene glycol, alkylated aromatics, such as alkylated naphthalenes, polyethylene glycol, trimethylol propane esters, neopentyl and pentaerythritol esters, di(2-ethylhexyl) sebacate, di(2-ethylhexyl) adipate, dibutyl phthalate, silicate esters, silanes, esters of phosphorus-containing acids, hydrogenated synthetic oils, chain-type polyphenyls, siloxanes and silicones (polysiloxanes) and alkyl-substituted diphenyl ethers typified by a butyl-substituted bis(p-phenoxy phenyl) ether and phenoxy phenylethers.

The lubricating oils and greases contemplated for blending with the reaction product can also contain other additives generally employed in lubricating compositions such as corrosion inhibitors, detergents, dispersants, extreme pressure agents, viscosity index improvers, demulsifiers, friction reducers, antiwear agents and the like. Typical examples of these additives include but are not limited to phenates, metallic phenates, sulfonates, metallic sulfonates, imides, heterocyclic compounds, polymeric acrylates or esters or amides or succinimides, amines, amides, esters, sulfurized olefins or esters or amides or imides, succinimides, succinate esters, metallic or non-metallic phosphorodithioates, olefin copolymers, styrene-diene copolymers, methacrylates, organic borates, metallic detergents such as those containing calcium or magnesium, arylamines, hindered phenols and the like.

It is also contemplated that the additives are useful in fuels. The fuels contemplated are liquid fuels, such as liquid hydrocarbon and liquid oxygenated fuels such as alcohols and ethers. The additives typically can be blended in a concentration from about 1 to about 1,000 pounds of additive per 1000 barrels of fuel, specifically about 25 to about 500 pounds of additive per 1,000 barrels of fuel. Liquid hydrocarbon fuels include gasoline, kerosene, jet fuels, gas oils, fuel oils, diesel oils and alcohol fuels which include methyl and ethyl alcohols and ethers such as diisopropyl ether (DIPE), methyl tert-butyl ether (MTBE), ethyl tert-butyl ether (ETBE), tertiary amyl methyl ether (TAME), and mixtures of any or all of the above.

Specifically, the fuel compositions contemplated include gasoline base stocks such as a mixture of hydrocarbons boiling in the gasoline boiling range which is from about 90° F. to about 450° F. This base fuel may consist of straight chains or branched chains, paraffins, cycloparaffins, olefins, aromatic hydrocarbons, or mixtures thereof. The base fuel can be derived from among others, straight run gasoline or naphtha, alkylate, reformate, polymer gasoline, natural gasoline or from catalytically cracked or thermally cracked hydrocarbons catalytically cracked reformed stock and mixtures thereof. The composition and octane level of the base fuel are not critical and any conventional motor fuel base can be employed in the practice of this invention.

Further examples of fuels of this type are petroleum distillate fuels having an initial boiling point from about 75° F. to about 400° F. and a final boiling point from about 250° F. to about 750° F. It should be noted in this respect that the term distillate fuels is not intended to be restricted to straight-run distillate fractions. Non-limiting examples of these distillate fuel oils include straight-run distillate fuel oils, alkylate, catalytically or thermally cracked (including hydrocracked) distillate fuel oils and mixtures thereof. Moreover, such fuel oils can be treated in accordance with well-known commercial methods, such as acid or caustic treatment, dehydrogenation, hydrotreating, solvent refining, clay treatment and the like.

Particularly contemplated among the distillate fuels are Nos. 1, 2 and 3 fuel oils used in heating and as diesel fuel oils, low sulfur diesel fuel, low aromatic diesel fuel, gasoline, turbine fuels, kerosene, jet combustion fuels and mixtures thereof.

Liquid oxygenated fuels may contain alcohols, ethers, and/or gasoline in amounts of 0 to 90 volume percent alcohol or ether in gasoline. An example of a fuel with a high alcohol concentration is M-85, 85% methanol and 15% gasoline. The fuel may be an alcohol-type fuel containing little or no hydrocarbon. Typical of such fuels are methanol, ethanol and mixtures of methanol and ethanol. The fuels which may be treated with the additive include gasohols which my be formed by mixing 90 to 95 volume percent gasoline with 5–10 volume percent of ethanol or methanol. A typical gasohol may contain 90 volume percent gasoline and 10 volume percent absolute ethanol. As mentioned above, oxygenated fuels may be made of a blend of gasoline and an ether. A typical blend of gasoline with methyl tert-butyl ether might include 85 volume percent gasoline and 15 volume percent ether.

The fuel compositions of the instant invention may additionally comprise any of the additives generally employed in fuel compositions. Thus, compositions of the instant invention may also contain conventional carburetor, fuel injector, and other detergents, anti-knock compounds such as tetraethyl lead, anti-icing additives, upper cylinder and fuel pump lubricity additives, corrosion inhibitors, dyes, pour point improvers, antioxidants, cetane improvers and the like.

EXAMPLE 1

Tolyltriazole-Oleyl Amine

Approximately 80 grams (0.6 mole) tolyltriazole (Sherwin Williams Co.), 167 grams (0.6 mole) oleyl amine (Armak-O, Armak Chemical Co.), 100 ml ethanol, and 100 ml toluene were charged to a 1 liter flask equipped with an agitator, Dean-Stark apparatus and dropping funnel. This mixture was stirred to a homogeneous mixture. Glyoxal (43.5 grams, 0.3 mole, 40% in water) was added dropwise and then stirred at room temperature for 12 hours. Water was then azeotropically removed by heating to 115° C. The dark brown product (261 grams) was isolated by filtration and removal of solvent under reduced pressure.

EXAMPLE 2

Tolyltriazole-N-oleyl-1,3-diaminopropane

Approximately 66.6 grams (0.5 mole) tolyltriazole, 175 grams (0.5 mole) N-oleyl-1,3-diaminopropane (Armak Chemical Co.), 100 ml ethanol, and 100 ml toluene were charged to a 1 liter flask equipped with an agitator, Dean-Stark apparatus, and dropping funnel. This mixture was stirred to a homogeneous mixture. Glyoxal (36.3 grams, 0.25 mole, 40% in water) was added dropwise and then stirred at room temperature for 12 hours. Water was then azeotropically removed by heating to 150° C. The orange product (237 grams) was isolated by filtration and removal of solvent under reduced pressure.

EXAMPLE 3

Tolyltriazole-Oleyl Amine-Oleic Acid

Approximately 53 grams (0.4 mole) tolyltriazole, 111 grams (0.4 mole) oleyl amine, 100 ml ethanol, and 100 ml toluene were charged to a 1 liter flask equipped with an agitator, Dean-Stark apparatus, and dropping funnel. This mixture was stirred to a homogeneous mixture. Glyoxal (29 grams, 0.2 mole, 40% in water) was added dropwise and then stirred at room temperature for 12 hours. Water was then azeotropically removed by heating to reflux temperatures of approximately 100°–120° C. While maintaining a temperature of less than or equal to 60° C., 56 grams (0.2 mole) oleic acid was added slowly. The reaction mixture was stirred at 60° C. for 1 hour. The orange product (243 grams) was isolated by filtration and removal of solvent under reduced pressure.

EXAMPLE 4

Tolyltriazole-N-oleyl-1,3-diaminopropane-Oleic Acid

Approximately 53 grams (0.4 mole) tolyltriazole, 140 grams (0.4 mole) N-oleyl-1,3-diaminopropane, 100 ml ethanol, and 100 ml toluene were charged to a 1 liter flask equipped with an agitator, Dean-Stark apparatus, and dropping funnel. This mixture was stirred to a homogeneous mixture. Glyoxal (29 grams, 0.2 mole, 40% in water) was added dropwise and then stirred at room temperature for 12 hours. Water was then azeotropically removed by heating to reflux temperatures of approximately 100°–120° C. After cooling to less than 60° C., 112 grams (0.4 mole) oleic acid was added slowly. The reaction mixture was stirred at 60° C. for 1 hour. The orange product (310 grams) was isolated by filtration and removal of solvent under reduced pressure.

EVALUATION OF PRODUCTS

The products of Examples 1–4 were blended into lubricants and evaluated for friction reduction activity using a Low Velocity Friction Apparatus (LVFA). The products of the examples were also blended into lubricants and into distillate fuels and were tested using the Four Ball Wear Test. The conditions of the tests are described below. The results of the LVFA tests are shown in Table 1, and the results of the Four Ball wear tests are shown in Table 2 and in Table 3. In the test using the Low Velocity Friction Apparatus (LVFA), two percent of the additive produced in each of the examples was dissolved in a standard mineral oil reference fluid blended with a dispersant/detergent/inhibitor performance package typical of an SG lube. Although evaluation of additives was performed in lubricant formulations, these results correlate well with expected frictional and fuel economy improvements when these same additives are used in fuels burned in internal combustion engines. For example, this test predicts the reduction in friction of the piston rings moving against the cylinder walls that have been wetted by fuel containing the additive. The resulting reduction in friction observed, if any, may translate into an improvement in economy of the fuel actually consumed. Additionally, these additives, when used in fuels, may actually help reduce wear of the internal combustion engine parts.

The Low Velocity Friction Apparatus (LVFA) is used to measure the coefficient of friction of test lubricants under various loads, temperatures, and sliding speeds. The LVFA consists of a flat SAE 1020 steel surface (diameter 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

The rubbing surfaces and 12–13 ml of test lubricant were placed on the LVFA. Coefficients of friction ($U_k$) were measured at 32–58 psi over a range of sliding speeds (0 to 30 ft./min.) at room temperature and at 250° F. Reported are results at 250° F., 48 psi., and at a sliding speed of zero ft./min. (static) and from the average of sliding speeds of 5 and 30 ft./min. (dynamic). The data are calculated as percent decrease in friction according to:

$$\frac{(U_k \text{ of oil alone}) - (U_k \text{ of additive plus oil})}{(U_k \text{ of oil alone})} \times 100$$

The percent change in the coefficients of friction of the test oil containing the example products relative to the test oil without example products is reported in Table 1. The value for the oil alone would be zero for the form of the data shown in the table.

TABLE 1

Friction Reducing Properties
Friction Test Results Using Low Velocity Friction Apparatus

| Test Sample | % Reduction in Coefficient of Friction | |
| --- | --- | --- |
| | Static | Dynamic |
| Base oil | — | — |
| Example 1 in base oil | 36 | 21 |
| Example 2 in base oil | 34 | 25 |
| Example 3 in base oil | 62 | 37 |
| Example 4 in base oil | 66 | 41 |

In the evaluation of antiwear activity associated with the additives of this invention combined with a distillate fuel base using the Four Ball wear test, the product of each of Examples 1 through 4 was blended into a low sulfur distillate fuel at 0.1 wt. % additive in the fuel. The results of the test are shown in Table 2.

In the Four Ball Wear Test, three stationary balls are placed in a lubricant cup and a lubricant containing the compound to be tested is added thereto, and a fourth ball is placed in a chuck mounted on a device which can be used to spin the ball at known speeds and loads. The distillate fuel based test samples were tested using half inch stainless steel balls of 52100 steel for thirty minutes under 10 kg load at 600 rpm and 122° F. The test is generally as described in ASTM test method D-2266.

K (as reported in Table 2 and in Table 3), the wear coefficient, is calculated from the wear volume, V, of the stationary balls. The wear volume is calculated from the wear scar diameter D in mm as follows:

$$V = (15.5\, D^3 - 0.0103 L) D \times 10^{-3} \text{ mm}^3$$

where L is the machine load in kg. This equation considers the elastic deformation of the steel balls.

WEAR COEFFICIENT K

Dimensionless K is defined as $$K = \frac{VH}{dW}$$

where

V=wear volume, mm$^3$

H=hardness 725 kg/mm$^2$ for 52100 steel d=(23.3 mm/rev) * (RPM) * (Time, min)

W=(0.408) * (Load in kg)

TABLE 2

Wear Reducing Properties
Four Ball Wear Test
½" Balls, 52100 Steel, 10 Kg., 600 RPM, 122° F., 30 min.

| Test Sample | K Factor |
| --- | --- |
| Base fuel | 38.4 |
| Example 1 in base fuel | 1.0 |
| Example 2 in base fuel | 1.3 |
| Example 3 in base fuel | 2.9 |
| Example 4 in base fuel | 3.9 |

In the evaluation of antiwear activity using the Four Ball wear test on the additives of this invention combined with a lubricant base, the product of each of Examples 1 through 4 was blended into a mineral base oil at 1 wt. % additive in the fuel. The lubricating oil based samples were tested using half inch stainless steel balls of 52100 steel for thirty minutes under 40 kg load at 1,800 rpm and 75° C. The results of the test are shown in Table 3. The wear coefficient, K, as defined above, was also used for this test using the different speed and load.

TABLE 3

Wear Reducing Properties
Four Ball Wear Test
½" Balls, 52100 Steel, 40 Kg., 1,800 RPM, 75° C., 30 min.

| Test Sample | K Factor |
| --- | --- |
| Base oil | 200 |
| Example 1 in base oil | 0.7 |
| Example 2 in base oil | 0.7 |
| Example 3 in base oil | 2.8 |
| Example 4 in base oil | 2.3 |

As shown above, the products of this invention induce an excellent reduction in friction and have excellent fuel and lubricant antiwear activity as indicated by LVFA and Four Ball test results.

The use of additive concentrations of glyoxal coupled nitrogen heterocycles/amines, and the products of carboxylic acids and carboxylic acid generating compounds with aldehyde/ketone/glyoxal coupled nitrogen heterocycles/ amines have been found to reduce friction and to provide metal antiwear protection in lubricants and fuels. These additives are expected to significantly reduce friction, improve fuel economy, reduce wear and extend engine life. These additives may also provide oxidative stability, high temperature stability, antifatigue, anticorrosion, antistaining, metal deactivation, cleanliness, extreme pressure, demulsifying, emulsifying, detergency, and dispersancy properties. They also have the potential to benefit fuel and lubricant properties by reducing hydrocarbon, carbon monoxide, and NO$_x$ emissions. Mild reaction conditions should translate to a relatively easy manufacturing process.

Obviously, many other variations and modifications of this invention as previously set forth may be made without departing from the spirit and scope of this invention as those skilled in the art readily understand. Such variations and modifications are considered part of this invention and within the purview and scope of the appended claims.

What we claim is:

1. A lubricant composition comprising a major amount of oil with viscosity suitable for use as a lubricant, grease produced therefrom, and a minor amount of an additive comprising the reaction product of:

(a) at least one nitrogen heterocycle;

(b) at least one amine;

(c) at least one dicarbonyl compound; and optionally, (d) at least one carboxyl compound or carboxyl generating compound.

2. The lubricant composition of claim 1, wherein the dicarbonyl compound comprises glyoxal and wherein the additive comprises the reaction product of the nitrogen heterocycle, the amine, the dicarbonyl, and the carboxyl compound or the carboxyl generating compound.

3. The lubricant composition according to claim 1 wherein the nitrogen heterocycle, the amine, and the dicarbonyl compound are first reacted together, and then the product of this reaction is post reacted with the carboxyl compound or carboxyl generating compound to produce the reaction product of claim 1.

4. The lubricant composition of claim 1 comprising selecting (a) the nitrogen heterocycle from the triazoles characterized by the following structural formula:

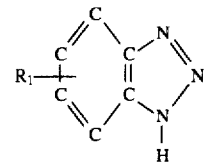

where R$_1$ is hydrogen or an alkyl group containing 1 to 60 carbon atoms or an alkyl group containing 2 to 60 carbon atoms and at least one heteroatom which is oxygen, sulfur, nitrogen, and combinations thereof;

(b) the amine from an alkyl amine, an alicyclic amine, a heterocyclic amine, an aliphatic diamine, an aliphatic triamine, an oxygenated amine, and mixtures thereof;

(c) the dicarbonyl from a dialdehyde or a glyoxal; and (d) the carboxyl compound from a carboxylic acid, carboxylic acid generating compound, or mixtures thereof.

5. The lubricant composition of claim 4 further comprising selecting the dicarbonyl from those with the structure:

where R$_2$ and R$_3$ are independently selected from hydrogen, a linear, branched or cyclical C$_1$–C$_{200}$ hydrocarbyl or hydrocarbylene or mixture thereof, and where R$_2$ and R$_3$ can additionally independently contain sulfur, oxygen, nitrogen and combinations thereof.

6. The lubricant composition of claim 4 further comprising selecting the alkyl amine from those with the structure:

where R$_4$, R$_5$, and R$_6$ are independently selected from hydrogen, linear, branched or cyclic C$_1$–C$_{200}$ hydrocarbyl or hydrocarbylene or a mixture thereof, at least one of $R_4$, $R_5$, or $R_6$ must be hydrogen, and where $R_4$, $R_5$, and $R_6$ can additionally independently contain sulfur, oxygen, nitrogen and combinations thereof.

7. The compound of claim 4 comprising further selecting the aliphatic diamine from a diamine which has the structural formula:

$$R_7-\underset{\underset{H}{|}}{N}-R_8-NH_2$$

where $R_7$ is an alkylene group containing 10 to 30 carbon atoms and $R_8$ is an alkylene group containing 2 to 4 carbon atoms.

8. The lubricant composition of claim 4 comprising further selecting the aliphatic triamine from a triamine which has the structural formula:

$$R_9NH(CH_2CH_2CH_2)NH(CH_2CH_2CH_2)NH_2$$

where $R_9$ is selected from hydrogen or $C_1$–$C_{20}$ linear, branched, or cyclic hydrocarbyl or hydrocarbylene group, and where $R_9$ can additionally contain sulfur, oxygen, nitrogen and combinations thereof.

9. The lubricant composition of claim 4 wherein the amine is an alkyl amine having the structure:

$$R_{10}NR_{11}(CH_2CH_2CH_2NH)_xCH_2CH_2CH_2NR_{12}R_{13}$$

where x is 0 to 10, and $R_{10}$, $R_{11}$, $R_{12}$, and $R_{13}$ are independently selected from hydrogen, $C_1$–$C_{200}$ linear, branched or cyclic hydrocarbyl or hydrocarbylene, and where $R_{10}$, $R_{11}$, $R_{12}$, and $R_{13}$ can additionally independently contain sulfur, oxygen, nitrogen and combinations thereof.

10. The lubricant composition of claim 4 in which the selected from the group consisting of pentylamine, hexylamine, octylamine, dioctylamine, dicocoamine, dioleylamine, 2-ethylhexylamine, isopropylamine, isobutylamine, diisobutylamine, bis(2-ethylhexyl)amine, 1,4-diaminocyclohexane, dicyclohexylamine, hexamethyleneimine or piperidine, morpholine, aminopropylmorpholine or aminoethylpiperazine, N-tallow-1,3-propylenediamine, N-oleyl- 1,3-propylenediamine, N-linoleyl-1,3-propylenediamine, N-stearyl- 1,3-propylenediamine, N-soya-1,3-propylenediamine, N-cocoyl- 1,3-diaminopropane, N-oleyl-1,3-diaminopropane, N-isostearyl- 1,3-propylenediamine, N-tallow-1,2-ethylenediamine, N-oleyl-1,2-ethylenediamine, N-linoleyl-1,2-ethylenediamine, N-stearyl-1,2-ethylenediamine, N-soya-1,2-ethylenediamine, N-cocoyl- 1,2-diaminoethane, N-oleyl-1,2-diaminoethane, N-isostearyl- 1,2-ethylenediamine, diethylene triamine or triamino propane, N,N'-di(2-aminoethyl)-amine, bis(hexamethylene) triamine, pentamethyl diethylenetriamine, 2,2-dimethyl-diethylenetriamine, N1-tert. butyl-1,2,3-triaminopropane, 2,2,5,5-tetramethyl diethylenetriamine, 1,3,6-triaminomethylhexane, 1,2, 3-triaminoethylpropane, 4-aminomethyloctamethylenediamine, 3,3'-diamino-dipropylamine, spermidine, 4,4'-diamino-dibutylamine, 6,6'diaminohexylamine, 2,4-bis(4-aminocyclohexylmethyl)cyclohexylamine, and mixtures thereof.

11. The lubricant composition of claim 4 in which the amine is an oxygenated amine selected from the group consisting of (a) 3-methoxypropylamine, 3-ethoxypropylamine, 3-propyloxypropylamine, 3-butyloxypropylamine, 3-octyloxypropylamine, 3-hexoxypropylamine, 3-heptoxypropylamine, 3-nonyloxypropylamine or 3-decyloxypropylamine;

(b) an ether diamine having the structural formula $$R_{14}{+}O-R_{15})_{\overline{a}}\underset{\underset{H}{|}}{N}-R_{16}-NH_2$$

where a is 1 to 20 and where $R_{14}$ is an alkyl group containing 4 to 20 carbon atoms, $R_{15}$ is an alkyl group containing 2 to 4 carbon atoms and $R_{16}$ is an alkyl group containing 2 to 10 carbon atoms;

(c) a polyether primary amine having the structure $$R_{17}-O-(C_2H_3(R_{18})O)_n-(C_3H_6)-NH_2$$

where $R_{17}$ is an alkyl-substituted phenyl group containing 14 to 26 carbon atoms, $C_6$ to $C_{30}$ alkyl group or $C_7$ to $C_{30}$ aralkyl group, n is an integer ranging from 2 to 10, and $R_{18}$ is independently an hydrogen atom or a methyl group; and (d) an hydroxyl-containing amine having the structure $$R_{19}-N\begin{matrix}{}^{\diagup(R_{20}O)_xH}\\{}_{\diagdown(R_{21}O)_yH}\end{matrix}$$

where x and y are integers from 1 to 10 and the sum of x+y is at least 1 and $R_{19}$ is selected from hydrogen or $C_1$–$C_{200}$ linear, branched, or cyclic hydrocarbyl or hydrocarbylene group, and where $R_{20}$ and $R_{21}$ are independently selected from $C_2$–$C_{10}$ hydrocarbylene oxide, and where $R_{19}$ can additionally contain at least one heteroatom which can be oxygen, sulfur, nitrogen and combinations thereof.

12. The lubricant composition of claim 4 in which the amine is an oxygenated amine selected from the group consisting of hexoxypropyl-1,3-propylenediamine, heptoxypropyl-1,3-propylenediamine, octoxypropyl-1,3-propylenediamine, nonyloxypropyl-1,3-propylenediamine and mixtures thereof.

13. The lubricant composition of claim 4 further comprising selecting the carboxylic acid from those with the structure:

$$R_{22}COOH \text{ or } R_{22}\begin{matrix}{}^{\diagup COOH}\\{}_{\diagdown COOH}\end{matrix} \text{ or } R_{22}\begin{matrix}{}^{\diagup COOH}\\-COOH\\{}_{\diagdown COOH}\end{matrix} \text{ or }$$

$$R_{22}\begin{matrix}\diagup\underset{\|}{C}\diagdown\\\diagdown\underset{\|}{C}\diagup\\{}^{O}\end{matrix}O \text{ or } HOOCR_{22}\begin{matrix}\diagup\underset{\|}{C}\diagdown\\\diagdown\underset{\|}{C}\diagup\\{}^{O}\end{matrix}O \text{ or } R_{22}{+}COOH)_4$$

where $R_{22}$, is selected from hydrogen, $C_1$–$C_{30}$ linear, branched or cyclic hydrocarbyl or hydrocarbylene or a mixture thereof, and where $R_{22}$ can additionally contain sulfur, oxygen, nitrogen or a combination thereof.

14. The lubricant composition of claim 4 wherein the nitrogen heterocycle consists essentially of tolyltriazole; the amine is selected from the group consisting of oleyl amine, N-oleyl-1,3,-diamino propane, and combinations thereof;

the dicarbonyl compound consists essentially of glyoxal; and the carboxyl compound consists essentially of oleic acid.

15. A lubricant composition comprising a major amount of oil with viscosity suitable for use as a lubricant or grease produced therefrom and a minor amount of an additive comprising a reaction product of:
   (a) at least one nitrogen heterocycle comprising tolyltriazole;
   (b) at least one amine selected from the group consisting of oleyl amine, N-oleyl-1,3,-diamino propane, and combinations thereof; and
   (c) glyoxal.

16. A method of making a lubricant comprising blending a major amount of oil with viscosity suitable for use as a lubricant or grease produced therefrom and a minor amount of an additive comprising a reaction product of:
   (a) at least one nitrogen heterocycle;
   (b) at least one amine;
   (c) glyoxal.

17. A method of making a lubricant comprising blending a major amount of oil with viscosity suitable for use as a lubricant or grease produced therefrom and a minor amount of an additive comprising a reaction product of:
   (a) at least one nitrogen heterocycle;
   (b) at least one amine;
   (c) at least one dicarbonyl compound; and optionally,
   (d) at least one carboxyl compound or carboxyl generating compound.

18. The method according to claim 17 wherein the additive comprises the reaction product of the nitrogen heterocycle, the amine, the dicarbonyl compound and the carboxyl compound.

19. The method according to claim 17 wherein the nitrogen heterocycle, the amine, and the dicarbonyl compound are first reacted together, and then the product of this reaction is post reacted with the carboxyl compound or carboxyl generating compound to produce the reaction product of claim 17.

20. The method according to claim 10 wherein the dicarbonyl comprises glyoxal.

21. A lubricant composition comprising a major amount of oil with viscosity suitable for use as a lubricant, grease produced therefrom, and a minor amount of an additive comprising the reaction product of:
   (a) at least one nitrogen heterocycle selected from a triazoles characterized by the following structural formula:

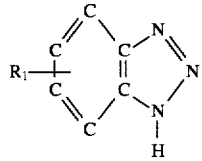

where $R_1$ is hydrogen or an alkyl group containing 1 to 60 carbon atoms or an alkyl group containing 2 to 60 carbon atoms and at least one heteroatom which is oxygen, sulfur, nitrogen, and combinations thereof;

(b) an oxygenated amine selected from the group consisting of
      (i) 3-methoxypropylamine, 3-ethoxypropylamine, 3-propyloxypropylamine, 3-butyloxypropylamine, 3-octyloxypropylamine, 3-hexoxypropylamine, 3-heptoxypropylamine, 3-nonyloxypropylamine, and 3-decyloxypropylamine;
      (ii) an ether diamine having the structural formula

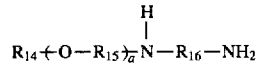

where a is 1 to 20 and where $R_{14}$ is an alkyl group containing 4 to 20 carbon atoms, $R_{15}$ is an alkyl group containing 2 to 4 carbon atoms and $R_{16}$ is an alkyl group containing 2 to 10 carbon atoms;
      (iii) a polyether primary amine having the structure

where $R_{17}$ is an alkyl-substituted phenyl group containing 14 to 26 carbon atoms, $C_6$ to $C_{30}$ alkyl group or $C_7$ to $C_{30}$ aralkyl group, n is an integer ranging from 2 to 10, and $R_{18}$ is independently an hydrogen atom or a methyl group; and
      (iv) an hydroxyl-containing amine having the structure

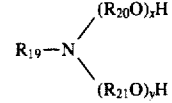

where x and y are integers from 1 to 10 and the sum of x+y is at least 1 and $R_{19}$ is selected from hydrogen or $C_1$–$C_{200}$ linear, branched, or cyclic hydrocarbyl or hydrocarbylene group, and where $R_{20}$ and $R_{21}$ are independently selected from $C_2$–$C_{10}$ hydrocarbylene oxide, and where $R_{19}$ can additionally contain at least one heteroatom which can be oxygen, sulfur, nitrogen and combinations thereof;
   (c) at least one dicarbonyl compound selected from an aldehyde or a glyoxal; and optionally,
   (d) at least one carboxyl compound selected from a carboxylic acid, carboxylic acid generating compound, or mixtures thereof.

22. The lubricant composition of claim 21 wherein the oxygenated amine is selected from the group consisting of hexoxypropyl-1,3-propylenediamine, heptoxypropyl-1,3-propylenediamine, octoxypropyl-1,3-propylenediamine, and nonyloxypropyl-1,3-propylenediamine.

* * * * *